US00PP11172P

United States Patent [19]

Glicenstein

[11] Patent Number: Plant 11,172

[45] Date of Patent: Jan. 4, 2000

[54] CHRYSANTHEMUM PLANT NAMED 'BOLD SOPHIA'

[75] Inventor: Leon Glicenstein, State College, Pa.

[73] Assignee: Yoder Brothers, Inc., Barberton, Ohio

[21] Appl. No.: 08/990,236

[22] Filed: Dec. 15, 1997

[51] Int. Cl.[7] ..... A01H 5/00

[52] U.S. Cl. ..... Plt./287

[58] Field of Search ..... Plt./76, 287

[56] References Cited

U.S. PATENT DOCUMENTS

P.P. 9,558 5/1996 VandenBerg ..... Plt./76
4,616,099 10/1986 Sparkes ..... 47/58

OTHER PUBLICATIONS

Broertjes, et al., 1980, "A Mutant of a Mutant of a . . . Irradiation of Progressive Radiation–Induced Mutants in a Mutation Breeding Programme with *Chrysanthemum* morifolium", Euphytica, 29:525–530.

Gosling, ed., 1979, "The Chrysanthemum Manual–6$^{th}$ edition", The National Chrysanthemum Society, London, Essex Telegraph Press, Ltd., pp. 329–336.

Broertjes, et al., 1978, "Application of Mutation Breeding Methods in the Improvement of Vegetatively Propagated Crops", Elsevier Sci. Pub. Co., New York, pp. 162–175.

Searle, et al., 1968, "Chrysanthemums the Year Round", Blanford Press, London, pp. 27–29, 320–327.

Chan, 1966, "Chrysanthemum and Rose Mutations Induced by X–rays", Am. Soc. Hort. Sci. Proc., pp. 613–620.

Broertjes, 1966, "Mutation Breeding of Chrysanthemums", Euphytica, 15:156–162.

Dowrick, et al., 1996, "The Induction of Mutations in Chrysanthemum Using X–and Gamma Radiation", Euphytica, 15: 204–210.

*Primary Examiner*—Howard J. Locker
*Attorney, Agent, or Firm*—C. A. Whealy

[57] ABSTRACT

A distinct cultivar of Chrysanthemum plant named 'Bold Sophia', characterized by its uniformly mounded plant habit; decorative-type inflorescences that are about 6.6 cm in diameter; attractive dark lavender ray florets; numerous inflorescences per plant; and excellent garden performance.

1 Drawing Sheet

The present invention relates to a new and distinct cultivar of Chrysanthemum plant, botanically known as *Dendranthema grandiflora* and referred to by the cultivar name Bold Sophia.

The new cultivar is a product of a mutation induction breeding program conducted by the inventor in Fort Myers, Fla., and Salinas, Calif. The objective of the breeding program is to create new garden type Chrysanthemum cultivars having with desirable inflorescence form and color and good garden performance.

The new cultivar originated by exposing 75 unrooted cuttings of the Chrysanthemum cultivar Sophia (disclosed in U.S. Plant Pat. No. 9,558) to an X-ray radiation level of 2,000 rads in February, 1994. Following the radiation treatment, the cuttings were rooted and terminal apices were removed (pinched) three times to promote lateral branch development. After lateral branches from the third pinch reached sufficient size, 956 terminal cuttings were harvested, planted and flowered in a controlled environment in Salinas, Calf. The cultivar Bold Sophia was discovered and selected by the inventor as a single flowering plant within this population in August, 1994. The selection of this plant was based on its desirable ray floret color, good form and excellent garden performance.

Asexual reproduction of the new cultivar by terminal cuttings taken in a controlled environment in Salinas, Calif., has shown that the unique features of this new Chrysanthemum are stable and reproduced true to type in successive generations.

The cultivar Bold Sophia has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Bold Sophia'. These characteristics in combination distinguish 'Bold Sophia' as a new and distinct cultivar:

1. Uniformly mounded plant habit.
2. Decorative-type inflorescences that are about 6.6 cm in diameter.
3. Attractive dark lavender ray florets.
4. Numerous inflorescences per plant.
5. Excellent garden performance.

Plants of the new Chrysanthemum have markedly darker lavender ray florets than plants of the parent cultivar, Sophia. In addition, plants of the new Chrysanthemum have slightly larger inflorescences than plants of the cultivar Sophia.

BRIEF DESCRIPTION OF THE PHOTOGRAPHS

The accompanying photographs illustrate the overall appearance of the new cultivar.

The photograph at the top of the sheet comprises a side perspective view of a typical flowering plant of 'Bold Sophia'.

The photograph at the bottom of the sheet comprises a close-up view of typical inflorescences of the cultivar 'Bold Sophia'. These photographs show the colors as true as it is reasonably possible to obtain in colored reproductions of its type. Floret and foliage colors in the photographs may differ from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown in Salinas, Calif., under conditions which approximate those generally used in commercial garden Chrysanthemum propduction. One unrooted cutting was directly stuck in a 15cm container and plants were grown in a greenhouse with night interruption lighting for two weeks during late May/early June. At end of the night interruption lighting period, plants were pinched (terminal apices removed). Three days later, plants were moved into an outdoor production area. Plants flowered about eight weeks later. Measurements and numerical values represent averages for typical flowering containers.

Botanical classification: *Dendranthema grandiflora* cultivar Bold Sophia.

Commercial classification: Decorative-type garden Chrysanthemum.

Parentage: Induced mutation of *Dendranthema grandiflora* cultivar Sophia, disclosed in U.S. Plant. Pat. No. 9,558.

Propagation:

*Type.*—Terminal tip cuttings.

*Time to rooting.*—Seven to ten days with soil temperatures of 21° C.

*Rooting habit.*—Fine, fibrous and well-branched.

Plant description:

*Appearance.*—Perennial herbaceous decorative-type garden Chrysanthemum. Inverted triangle. Stems initially upright, the spreading giving a uniformly mounded appearance to the plant. Freely branching; about eight lateral branches develop after removal of terminal apex (pinching). Numerous secondary lateral branches develop at every node.

*Plant height.*—About 29 cm.

*Foliage description.*—Leaf arrangement: Alternate. Length: About 9 cm. Width: About 7 cm. Apex: Mucronate. Base: Attenuate. Margin: Palmately lobed, sinuses parallel. Texture: Upper and lower surfaces slightly pubescent. Veins prominent on lower surface. Petiole length: About 2.3 cm. Color: Young foliage upper surface: 147A. Young foliage lower surface: 147B/147C. Mature foliage upper surface: 147A. Mature foliage lower surface: Close to 147B. Venation upper surface: 147B. Venation lower surface: 147B.

Inflorescence description:

*Appearance.*—Decorative-type inflorescence form with oblong-shaped ray florets. Inflorescences borne on terminals above foliage, arising from leaf axils. Disk and ray florets arranged acropetally on a capitulum. One inflorescence per terminal with numerous inflorescences per plant.

*Flowering response.*—Under natural conditions, plant flowers in the early autumm. Plants exposed to 1.5 to 2 weeks of long day/short night conditions after planning followed by short day/long night conditions flower about 53 days later.

*Inflorescence size.*—Diameter: About 6.6 cm. Depth (height): About 2 cm. Diameter of disc: About 3 mm.

*Ray florets.*—Shape: Oblong, initially cupped, then recurved. Length: About 3.2 cm. Width: About 1 cm. Apex: Rounded to dentate. Margin: Entire Texture: Smooth, glabrous. Orientation: Horizontal to recurved with development. Number of ray florets per inflorescence: About 290. Color: When opening: 72A/72b. Opened inflorescence: Upper surface: 77B to 70B fading to 75A. Lower surface: 75A/75B.

*Disc florets.*—Shape: Tubular, apex dentate. Length: About 6 mm. Width: Apex: About 1.5 mm. Base: About 1 mm. Number of disc florets per inflorescence: About five. Color: Immature: 154A. Mature: Apex: 13A. Base: White.

*Peduncle.*—Aspect: Flexible, angled outwardly about 40° to the stem. Length: First peduncle: About 5 cm. Fourth peduncle: About 6.5 cm. Texture: Pubescent. Color: Close to 147B.

*Reproductive organs.*—Androecium: Present on disc florets only. Pollen color: 13A. Amount of pollen: Moderate to low. Gynoecium: Present on both ray and disc florets.

Disease resistance: No known Chrysanthemum diseases observed to date on plants grown under commercial production conditions.

Seed production: Seed production has not been observed.

It is claimed:

1. A new and distinct cultivar of Chrysanthemum plant named 'Bold Sophia', as illustrated and described.

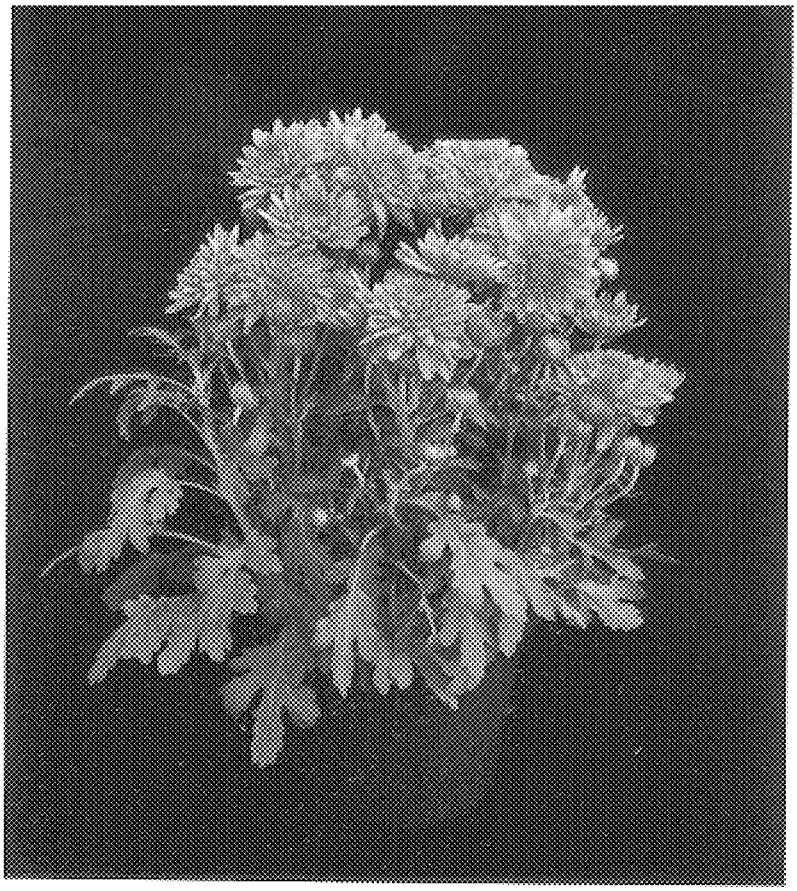
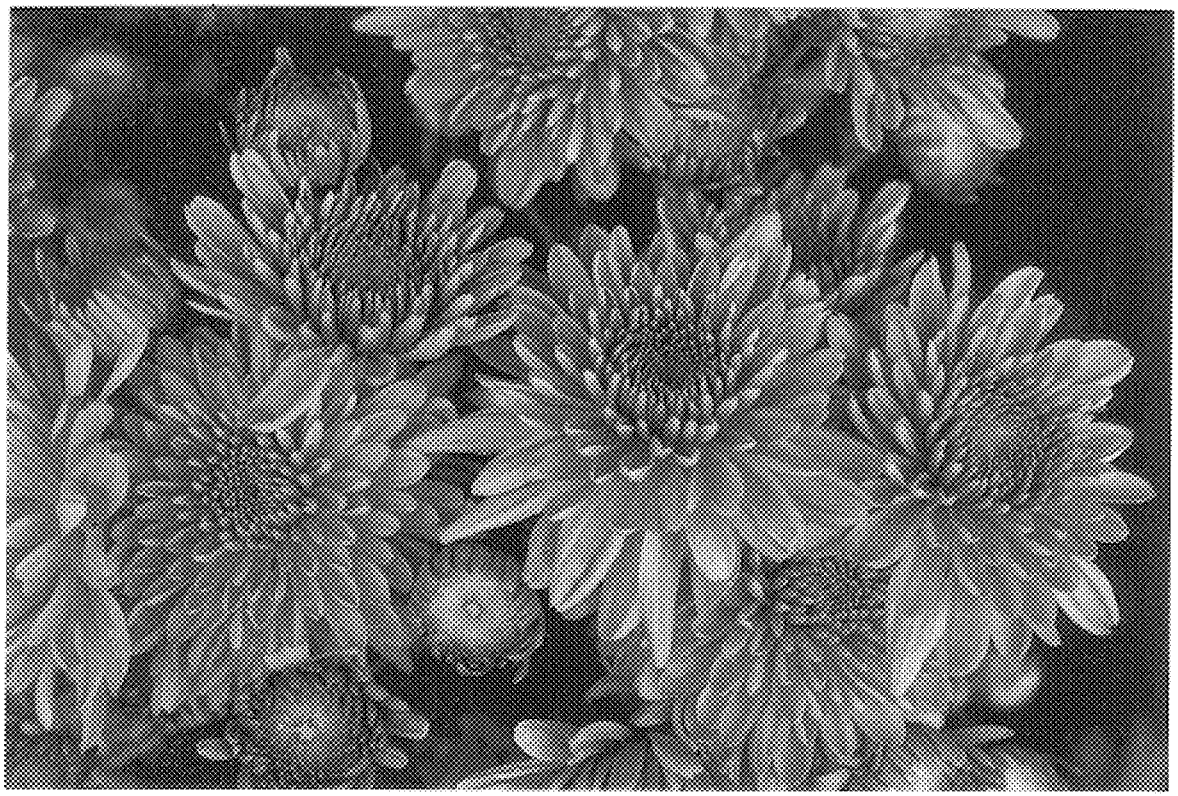

* * * * *